US010036056B2

(12) United States Patent
Chan et al.

(10) Patent No.: US 10,036,056 B2
(45) Date of Patent: Jul. 31, 2018

(54) CATALYTIC NUCLEIC ACID AND GOLD NANOPARTICLES FOR DETECTION OF BIOMOLECULES

(71) Applicant: THE GOVERNING COUNCIL OF THE UNIVERSITY OF TORONTO, Toronto (CA)

(72) Inventors: Warren Che Wor Chan, Toronto (CA); Kyrylo Zagorovsky, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 14/897,622

(22) PCT Filed: Jun. 12, 2013

(86) PCT No.: PCT/CA2013/050442
§ 371 (c)(1),
(2) Date: Dec. 10, 2015

(87) PCT Pub. No.: WO2014/197965
PCT Pub. Date: Dec. 18, 2014

(65) Prior Publication Data
US 2016/0108465 A1    Apr. 21, 2016

(51) Int. Cl.
*C12Q 1/6823* (2018.01)
*C12Q 1/6825* (2018.01)

(52) U.S. Cl.
CPC ......... *C12Q 1/6825* (2013.01); *C12Q 1/6823* (2013.01); *Y02A 50/58* (2018.01)

(58) Field of Classification Search
CPC . C12Q 1/68; C12M 1/34; C07H 21/04; C40B 30/04; G01N 33/54346; Y10S 277/942
See application file for complete search history.

(56) References Cited

U.S. PATENT DOCUMENTS 5,670,637 A    9/1997   Gold et al.
2003/0049857 A1*   3/2003   Chan ............... C01N 33/54366
                                                 436/164

(Continued)

FOREIGN PATENT DOCUMENTS

WO    WO2005001113    *   1/2005

OTHER PUBLICATIONS

Schlosser, K. & Li, Y. (2010). A Versatile Endoribonuclease Mimic Made of DNA: Characteristics and Applications of the 8-17 RNA-Cleaving DNAzyme. ChemBioChem, 11(7), 866-879.

(Continued)

*Primary Examiner* — Narayan Bhat
(74) *Attorney, Agent, or Firm* — Foley & Lardner LLP; Antoinette F. Konski; Peter Diez

(57) ABSTRACT

The present invention relates to catalytic nucleic acid molecule signal amplification combined with surface plasmon properties of gold nanoparticles to achieve simple and sensitive colorimetric detection of biological targets. The assays of the present invention have about 50 pM sensitivity without the need for purification steps, can detect multiple targets in parallel, and is easily adaptable to new targets. The methods of the present invention are capable of rapid detection of genetic targets for gonorrhea, syphilis, malaria, and hepatitis B infections.

13 Claims, 4 Drawing Sheets

(56) References Cited

U.S. PATENT DOCUMENTS

| | | | | |
|---|---|---|---|---|
| 2005/0037397 A1* | 2/2005 | Mirkin | ............... | B82Y 30/00 |
| | | | | 506/4 |
| 2007/0231810 A1* | 10/2007 | Todd | ............... | C12N 15/111 |
| | | | | 435/6.18 |
| 2010/0119610 A1* | 5/2010 | Schoen | ............ | A61K 31/7088 |
| | | | | 424/490 |

OTHER PUBLICATIONS

Santoro, S.W. & Joyce, G.F. (1997). A general purpose RNA-cleaving DNA enzyme. Proceedings of the national academy of sciences, 94(9), 4262-4266.

Breaker, R.R. & Joyce, G.F. (1994). A DNA enzyme that cleaves RNA. Chemistry & biology, 1(4), 223-229.

Mokany, E. et al. (2009). MNAzymes, a versatile new class of nucleic acid enzymes that can function as biosensors and molecular switches. Journal of the American Chemical Society, 132(3), 1051-1059.

Kolpashchikov, D.M. (2007). A binary deoxyribozyme for nucleic acid analysis. ChemBioChem, 8(17), 2039-2042.

Perrault, S.D. & Chan, W.C. (2009). Synthesis and surface modification of highly monodispersed, spherical gold nanoparticles of 50-200 nm. Journal of the American Chemical Society, 131(47), 17042-17043.

Hurst, S.J. et al (2006). Maximizing DNA loading on a range of gold nanoparticle sizes. Analytical chemistry, 78(24), 8313-8318.

Zhao, W. et al. (2008). Enzymatic cleavage of nucleic acids on gold nanoparticles: a generic platform for facile colorimetric biosensors. Small, 4(6), 810-816.

Liu, J. & Lu, Y. (2003). A colorimetric lead biosensor using DNAzyme-directed assembly of gold nanoparticles. Journal of the American Chemical Society, 125(22), 6642-6643.

Mazumdar, D. et al. (2010). Easy-to-use dipstick tests for detection of lead in paints using non-cross-linked gold nanoparticle-DNAzyme conjugates. Chem. Commun., 46(9), 1416-1418.

Lee, J.H. et al. (2008). Highly sensitive and selective colorimetric sensors for uranyl ($UO_2{}^{2+}$): Development and comparison of labeled and label-free DNAzyme-gold nanoparticle systems. Journal of the American Chemical Society, 130(43), 14217-14226.

Liu, J. & Lu, Y. (2004). Adenosine-dependent assembly of aptazyme-functionalized gold nanoparticles and its application as a colorimetric biosensor. Analytical Chemistry, 76(6), 1627-1632.

Elghanian, R. et al. (1997). Selective colorimetric detection of polynucleotides based on the distance-dependent optical properties of gold nanoparticles. Science, 277(5329), 1078-1081.

Sato, K. et al. (2005). Non-cross-linking gold nanoparticle aggregation as a detection method for single-base substitutions. Nucleic acids research, 33(1), e4-e4.

* cited by examiner

SEQUENCE LISTING

```
<160> NUMBER OF SEQ ID NOS: 30

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide: Agg1/A
<220> FEATURE:
<221> NAME/KEY: misc_feature
<223> OTHER INFORMATION: 5'-thiol-modified

<400> SEQUENCE: 1
aaaaaaaaaa cctatcgacc atgct                                       25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide: AggGon/A
<220> FEATURE:
<221> NAME/KEY: misc_feature
<223> OTHER INFORMATION: 5'-thiol-modified

<400> SEQUENCE: 2
aaaaaaaaaa taacaataat ccctc                                       25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide: AggMal/A
<220> FEATURE:
<221> NAME/KEY: misc_feature
<223> OTHER INFORMATION: 5'-thiol-modified

<400> SEQUENCE: 3
aaaaaaaaaa atggccgatg tatgt                                       25
```

```
<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide: AggSyph/A
<220> FEATURE:
<221> NAME/KEY: misc_feature
<223> OTHER INFORMATION: 5'-thiol-modified

<400> SEQUENCE: 4
aaaaaaaaaa cgagtgagtg cgacg                                          25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide: AggHBV/A
<220> FEATURE:
<221> NAME/KEY: misc_feature
<223> OTHER INFORMATION: 5'-thiol-modified

<400> SEQUENCE: 5
aaaaaaaaaa ttattggtgt tactc                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide: Agg1/B
<220> FEATURE:
<221> NAME/KEY: misc_feature
<223> OTHER INFORMATION: 3'-thiol-modified

<400> SEQUENCE: 6
gcgctagagt cgtttaaaaa aaaaa                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide: AggGon/B
<220> FEATURE:
<221> NAME/KEY: misc_feature
<223> OTHER INFORMATION: 3'-thiol-modified

<400> SEQUENCE: 7
atccttatca atattaaaaa aaaaa                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide: AggMal/B
<220> FEATURE:
<221> NAME/KEY: misc_feature
<223> OTHER INFORMATION: 3'-thiol-modified

<400> SEQUENCE: 8
agaggaaagt aggctaaaaa aaaaa                                          25

<210> SEQ ID NO 9
<211> LENGTH: 25
<212> TYPE: DNA
<213> ORGANISM: Artificial Sequence
```

```
<220> FEATURE:
<223> OTHER INFORMATION: Synthetic oligonucleotide: AggSyph/B
<220> FEATURE:
<221> NAME/KEY: misc_feature
<223> OTHER INFORMATION: 3'-thiol-modified

<400> SEQUENCE: 9
ggtggcttac agtcaaaaaa aaaaa                                    25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide: AggHBV/B
<220> FEATURE:
<221> NAME/KEY: misc_feature
<223> OTHER INFORMATION: 3'-thiol-modified

<400> SEQUENCE: 10
tgtagggcat gtagtaaaaa aaaaa                                    25

<210> SEQ ID NO 11
<211> LENGTH: 54
<212> TYPE: DNA
<213> ORGANISM: Artificial Sequence
<220> FEATURE:
<223> OTHER INFORMATION: Synthetic oligonucleotide: Linker1

<400> SEQUENCE: 11
agcatggtcg ataggtaagg tttcctcguc cctgggcata aacgactcta gcgc    54

<210> SEQ ID NO 12
<211> LENGTH: 53
<212> TYPE: DNA
<213> ORGANISM: Artificial Sequence
<220> FEATURE:
<223> OTHER INFORMATION: Synthetic oligonucleotide: LinkerGon

<400> SEQUENCE: 12
gagggattat tgttatactc actatgugga agagatgtaa tattgataag gat     53

<210> SEQ ID NO 13
<211> LENGTH: 56
<212> TYPE: DNA
<213> ORGANISM: Artificial Sequence
<220> FEATURE:
<223> OTHER INFORMATION: Synthetic oligonucleotide: LinkerMal

<400> SEQUENCE: 13
acatacatcg gccattcgca aaccatagug agaacacgtg tagcctactt tcctct  56

<210> SEQ ID NO 14
<211> LENGTH: 55
<212> TYPE: DNA
<213> ORGANISM: Artificial Sequence
<220> FEATURE:
<223> OTHER INFORMATION: Synthetic oligonucleotide: LinkerSyph

<400> SEQUENCE: 14
cgtcgcactc actcgttgtg acactatgua gcgatcttgt tgactgtaag ccacc   55

<210> SEQ ID NO 15
<211> LENGTH: 55
<212> TYPE: DNA
<213> ORGANISM: Artificial Sequence
<220> FEATURE:
```

<223> OTHER INFORMATION: Synthetic oligonucleotide: LinkerHBV

<400> SEQUENCE: 15
gagtaacacc aataattgct ggacagagug tataggattt actacatgcc ctaca        55

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide: Mz1/A

<400> SEQUENCE: 16
agctgctgcc cgtgctggtg acaacgagag gaaacctt        38

<210> SEQ ID NO 17
<211> LENGTH: 37
<212> TYPE: DNA
<213> ORGANISM: Artificial Sequence
<220> FEATURE:
<223> OTHER INFORMATION: Synthetic oligonucleotide: MzGon/A

<400> SEQUENCE: 17
tgccaatatc ggcggccgat gacaacgaat agtgagt        37

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide: MzMal/A

<400> SEQUENCE: 18
aactcaatca tgactacccg acaacgatat ggtttgcg        38

<210> SEQ ID NO 19
<211> LENGTH: 38
<212> TYPE: DNA
<213> ORGANISM: Artificial Sequence
<220> FEATURE:
<223> OTHER INFORMATION: Synthetic oligonucleotide: MzSyph/A

<400> SEQUENCE: 19
gtccatcggc aaacacgtca acaacgaata gtgtcaca        38

<210> SEQ ID NO 20
<211> LENGTH: 38
<212> TYPE: DNA
<213> ORGANISM: Artificial Sequence
<220> FEATURE:
<223> OTHER INFORMATION: Synthetic oligonucleotide: MzHBV/A

<400> SEQUENCE: 20
caggaggttg gtgagtgatt acaacgatct gtccagca        38

<210> SEQ ID NO 21
<211> LENGTH: 39
<212> TYPE: DNA
<213> ORGANISM: Artificial Sequence
<220> FEATURE:
<223> OTHER INFORMATION: Synthetic oligonucleotide: Mz1/B

<400> SEQUENCE: 21
tgcccaggga ggctagctcc attgccccat gtgaagtca        39

```
<210> SEQ ID NO 22
<211> LENGTH: 39
<212> TYPE: DNA
<213> ORGANISM: Artificial Sequence
<220> FEATURE:
<223> OTHER INFORMATION: Synthetic oligonucleotide: MzGon/B

<400> SEQUENCE: 22
catctcttcc aggctagcta cggtacctga agaataagc                                    39

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide: MzMal/B

<400> SEQUENCE: 23
cacgtgttct caggctagct tctgttatga acacttaatt tt                                42

<210> SEQ ID NO 24
<211> LENGTH: 41
<212> TYPE: DNA
<213> ORGANISM: Artificial Sequence
<220> FEATURE:
<223> OTHER INFORMATION: Synthetic oligonucleotide: MzSyph/B

<400> SEQUENCE: 24
caagatcgct aggctagcta ctgcagcatc catcagagtc t                                 41

<210> SEQ ID NO 25
<211> LENGTH: 41
<212> TYPE: DNA
<213> ORGANISM: Artificial Sequence
<220> FEATURE:
<223> OTHER INFORMATION: Synthetic oligonucleotide: MzHBV/B

<400> SEQUENCE: 25
aatcctatac aggctagctg gaggttgggg actgcgaatt t                                 41

<210> SEQ ID NO 26
<211> LENGTH: 47
<212> TYPE: DNA
<213> ORGANISM: Artificial Sequence
<220> FEATURE:
<223> OTHER INFORMATION: Synthetic oligonucleotide: AF-1

<400> SEQUENCE: 26
cagtgacttc acatggggca atggcaccag cacgggcagc agctggc                           47

<210> SEQ ID NO 27
<211> LENGTH: 44
<212> TYPE: DNA
<213> ORGANISM: Artificial Sequence
<220> FEATURE:
<223> OTHER INFORMATION: Synthetic oligonucleotide: Gon

<400> SEQUENCE: 27
tgcttattct tcaggtaccg tcatcggccg ccgatattgg caac                              44

<210> SEQ ID NO 28
<211> LENGTH: 50
<212> TYPE: DNA
<213> ORGANISM: Artificial Sequence
<220> FEATURE:
<223> OTHER INFORMATION: Synthetic oligonucleotide: Mal
```

```
<400> SEQUENCE: 28
aaaattaagt gttcataaca gacgggtagt catgattgag ttcattgtgt            50

<210> SEQ ID NO 29
<211> LENGTH: 46
<212> TYPE: DNA
<213> ORGANISM: Artificial Sequence
<220> FEATURE:
<223> OTHER INFORMATION: Synthetic oligonucleotide: Syph

<400> SEQUENCE: 29
ggagactctg atggatgctg cagttgacgt gtttgccgat ggacag                46

<210> SEQ ID NO 30
<211> LENGTH: 54
<212> TYPE: DNA
<213> ORGANISM: Artificial Sequence
<220> FEATURE:
<223> OTHER INFORMATION: Synthetic oligonucleotide: HBV

<400> SEQUENCE: 30
gccaaaattc gcagtcccca acctccaatc actcaccaac ctcctgtcct ccaa       54
```

CATALYTIC NUCLEIC ACID AND GOLD NANOPARTICLES FOR DETECTION OF BIOMOLECULES

CROSS-REFERENCE TO RELATED APPLICATIONS

This application is a national stage application under 35 U.S.C. § 371 of International Application No. PCT/CA2013/050442, filed Jun. 12, 2013, the content of which is incorporated herein by reference in its entirety.

FIELD OF THE INVENTION

The present disclosure relates to the field of detection of biological molecules. More particularly, the present invention relates to methods of detecting target biological molecules in a sample with the use of catalytic nucleic acid molecules and gold nanoparticles.

BACKGROUND OF THE INVENTION

The development of simple, cost-effective, sensitive, and specific point-of-care (POC) diagnostics represents a major challenge in the 21st century. [1] The spread of infectious diseases has caused significant losses in global economy and life. A method to control the spread of diseases is to detect the pathogens early at POC, and to administer proper treatment or quarantine. [2] Detection of DNA as biomarkers is currently a widely used technique for pathogenic detection. [3] Quantitative PCR (qPCR) is the method of choice, since it includes an enzymatic signal amplification step to achieve highly sensitive and specific detection of genetic targets. [4] However, qPCR requires expensive equipment and highly trained personnel, limiting the technique use to medical laboratories. There is a strong need to develop cheaper and simpler methods for detecting DNA targets and/or other biological targets. [5]

DNAzyme is a synthetic DNA enzyme that can catalyze the cleavage of another nucleic acid molecule. [6-8] Since the catalysis is carried out with multiple turnover, DNAzyme introduces an enzymatic amplification step into the experimental setup. [9] This amplification is performed without the need for protein components, which are costly and have low thermal and storage stability. While initially designed to detect $Pb^{2+}$ and other divalent cations, [10-19] a number of modifications have been reported that allow DNAzyme to detect biomolecular targets. [9,20-27] Two main approaches were used to implement detection of genetic targets. The first method utilizes competitive activation of peroxidase-mimicking DNAzyme, which can catalyze production of colorimetric or chemiluminescent product. [28] In the second, more sensitive approach, a similar strategy was followed by a number of groups to implement detection of genetic targets by splitting the DNAzyme into inactive components, which could be reactivated by the target binding. [9, 23-25, 29] However, these studies used fluorescence as the readout, which is not an optimal detection modality for POC applications since it requires access to fairly complex fluorometer apparatus. An alternative method using the colorimetric readout of gold nanoparticles (GNPs) has been reported for detection of metal ions, adenosine and cocaine. [10-14, 16-18, 20, 21] The wavelength at which GNPs absorb light is dependent on whether they are in a monodispersed or aggregated state. [30] Since the GNP solutions in monodispersed or aggregated states are easily distinguishable by their respective red or purple colors, this approach provides clear colorimetric results that can be visualized by the naked eye. [31]

As such, an object of the invention is to overcome the above limitations by combining DNAzyme technology with GNPs to engineer a simple point-of-care diagnostic platform that can be used in remote settings. [32, 33]

Further and other objects of the invention will be realized from the following Summary of the Invention, the Discussion of the Invention and the embodiments and Examples thereof.

SUMMARY OF THE INVENTION

The present invention relates to the combined colorimetric coupling of surface plasmons of gold nanoparticles with DNAzyme signal amplification technology to engineer a fast and simple detection platform for genetic targets with a simple colorimetric readout. The inventiveness of this disclosure includes the integration of these two emerging technologies for detection of biological targets that may be used for point-of-care analysis of infectious disease targets.

As such, in one embodiment, the present invention provides for a method of detecting the presence of a biological target in a sample. The method, in one embodiment, includes: (a) contacting the sample with: (i) an un-catalyzed nucleic acid substrate, (ii) a catalytic nucleic acid, the catalytic nucleic acid configured for catalyzing the substrate solely in the presence of the target, and (iii) GNPs, the GNPs functionalized with a linking moiety for assembling with the un-catalyzed nucleic acid substrate; and (b) analyzing the sample to determine whether the GNPs are in a substantially dispersed form or in an assembled form with the un-catalyzed nucleic acid substrate, wherein the GNPs being in the substantially dispersed form is indicative that the target is present in the sample.

In one embodiment of the method for detecting a biological target in a sample, (i) and (ii) are first added to the sample for a sufficient amount of time at a suitable temperature, and then (iii) is added to the sample.

In another embodiment of the method for detecting a biological target in a sample, the catalytic nucleic acid are provided as pre-catalytic nucleic acid subunits, each pre-catalytic nucleic acid subunit including a sensor domain configured for binding to at least a portion of the target, and a catalytic domain which catalyzes the un-catalyzed nucleic acid substrate solely when the target is bound to the sensor domain.

In another embodiment of the method for detecting a biological target in a sample, the GNPs are functionalized with nucleic acid strands that hybridize with a 3' end and a 5' end of the un-catalyzed nucleic acid substrate for assembling.

In another embodiment of the method for detecting a biological target in a sample, in the assembled form the GNPs turn the sample to a first color, and in the substantially dispersed form the GNPs turn the sample to a second color, and wherein step (b) of the method includes determining the color of the sample. Detecting the second color is indicative of the presence of the target in the sample.

In another embodiment of the method for detecting a biological target in a sample, the un-catalyzed nucleic acid substrate, the catalytic nucleic acid and the GNPs are functionalized to be target specific.

In one embodiment, the present invention provides for a method of simultaneously detecting the presence of a number of different biological targets of interest in a sample. In one embodiment, the method includes: (a) mixing the sample suspected of having the number of different biological targets with target-specific sets of (i) target-specific un-catalyzed nucleic acid substrates and (ii) target-specific catalytic nucleic acids, the catalytic nucleic acids in each target-specific set configured for catalyzing the un-catalyzed substrate solely in the presence of the target; (b) contacting the mixture of step (a) with separate target-specific populations of GNPs, the GNPs in each target-specific population functionalized with a linking moiety for assembling with its corresponding target-specific un-catalyzed nucleic acid substrate; and (c) determining for each separate target-specific population of GNPs whether the target-specific GNPs are in an assembled form with the corresponding target specific un-catalyzed substrate or in a substantially dispersed form, wherein the target-specific GNPs being in the substantially dispersed form in one population is indicative that the target corresponding to this population of target-specific GNP is present in the sample.

In one embodiment of the method of simultaneously detecting the presence of a number of different biological targets of interest in a sample, the catalytic nucleic acid are provided as pre-catalytic nucleic acid subunits, each pre-catalytic nucleic acid subunit including a sensor domain for specifically binding to one of the number of different targets, and a catalytic domain configured for catalyzing its corresponding target-specific un-catalyzed nucleic acid substrate solely when the corresponding target is bound to the sensor arm.

In another embodiment of the method of simultaneously detecting the presence of a number of different biological targets of interest in a sample of the present invention, in the assembled form the GNPs turn the sample to a first color, and in the substantially dispersed form the GNPs turn the sample to a second color, and wherein step (c) of the method includes determining the color of the sample for each population of GNPs. Detecting the second color in one population of GNPs is indicative of the presence of the target of this population of GNPs in the sample.

In one embodiment of the method of any the previous embodiments, the method further includes spotting the sample onto thin layer chromatography (TLC) plates for visual detection. In one aspect of this embodiment, the method further includes storing the TLC for later viewing.

In another embodiment of the method of any the previous embodiments, the method further comprises a spectroscopic measurement of the UV-visible spectroscopic shift of peak absorbance.

In another embodiment of the method of any the previous embodiments, the catalytic nucleic acid and the un-catalyzed nucleic acid substrate are provided as a lyophilized mixture.

In another embodiment of the method of any the previous embodiments, the catalytic nucleic acid, the un-catalyzed nucleic acid substrate and the GNPs are provided lyophilized.

In yet another embodiment, the present invention provides for a kit for detecting a biological target of interest in a sample. The kit, in one embodiment, includes: (a) an un-catalyzed nucleic acid substrate, (b) catalytic nucleic acid capable catalyzing the un-catalyzed substrate solely in the presence of the target, and (c) GNPs functionalized with a linking moiety to assemble with the un-catalyzed nucleic acid substrate.

In one embodiment of the kit, the catalytic nucleic acid are provided as pre-catalytic nucleic acid subunits, each pre-catalytic nucleic acid subunit including a sensor domain for binding to at least a portion of the target, and a catalytic domain which catalyzes the un-catalyzed nucleic acid substrate solely when the target is bound to the sensor domain.

In another embodiment of the kit, GNPs assembled with the un-catalyzed nucleic acid substrate turn the sample to a first color, and GNPs in a substantially dispersed form turn the sample to a second color.

In another embodiment of the kit, the un-catalyzed nucleic acid substrate and the catalytic nucleic acid are in a lyophilized mixture.

In another embodiment of the kit, the GNPs, un-catalyzed nucleic acid substrate and the catalytic nucleic acid are in a lyophilized mixture.

In another embodiment of the kit, the kit further includes ingredients necessary for optimal activity of the catalytic arm.

In another embodiment of the kit, the kit further includes a TLC.

BRIEF DESCRIPTION OF THE DRAWINGS

Embodiments will now be described, by way of example only, with reference to the drawings, in which.

DETAILED DESCRIPTION OF THE INVENTION

Definitions

Figure 1:
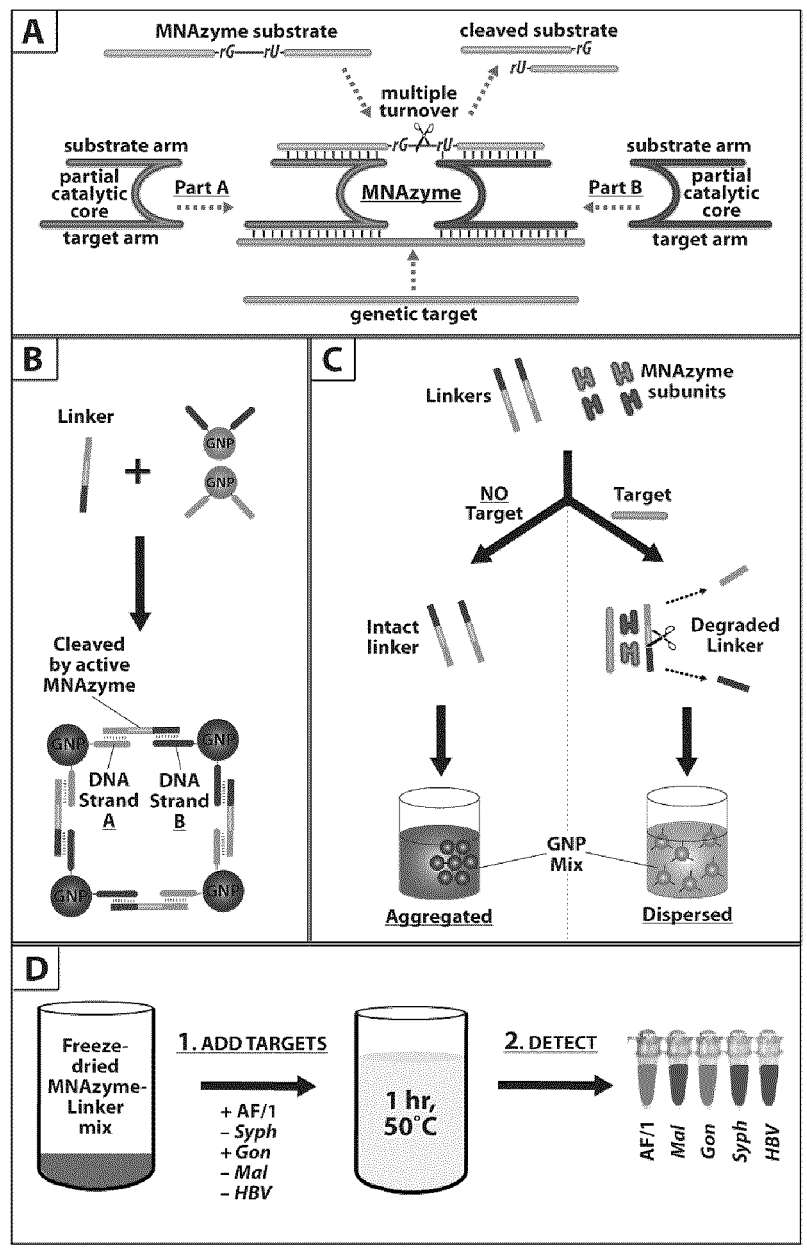
FIG. 1: Panel A—Mechanism of MNAzyme catalysis. Adapted with permission from [9]. Copyright 2009 American Chemical Society. Panel B—GNP aggregate formation. Linker hybridizes to DNA strands A and B, crosslinking the two sets of GNPs and turning solution purple. Panel C—MNAzyme assay outline. Target activated MNAzyme degrades Linker DNA, preventing GNP aggregate formation. In the absence of the target Linkers remain intact and cross-link GNPs (as in B); the solution turns purple. Panel D—Schematic depicting how the assay will be conducted at point-of-care to analyze multiple targets in parallel.

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

The singular form "a", "an", and "the" includes plural references unless the context clearly dictates otherwise.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

"Catalytic nucleic acid molecule", "catalytic nucleic acid", and "catalytic nucleic acid sequence" are equivalent, and each shall mean a DNA molecule or DNA-containing molecule (also known in the art as a "DNAzyme") or an RNA or RNA-containing molecule (also known in the art as a "ribozyme") which specifically recognizes a distinct substrate and catalyzes the chemical modification of this substrate. The nucleic acid bases in the DNAzymes and ribozymes can be the bases A, C, G, T and U, as well as derivatives thereof known in the art [PCR Systems, Reagents and Consumables. Perkin Elmer Catalogue 1996-1997. Roche Molecular Systems, Inc., Branchburg, N.J., USA.]. Each catalytic nucleic acid molecule may be divided into pre-catalytic nucleic acid subunits that are not capable of catalyzing the chemical modification of the substrate.

"GNP" or "GNPs" refer to gold nanoparticle(s).

"GNP-A" refers to a GNP functionalized with a linking moiety A, which may be a nucleic acid strand A, as explained bellow. "GNP-B" refers to a GNP functionalized with a linking moiety B, which may be nucleic acid strand B, as explained bellow. "GNP-AB" refers to a GNP functionalized with both linking moieties A and B, which may be nucleic acid strand A and nucleic acid strand B, as explained bellow. Accordingly, at least three populations of GNP may exist: GNP-A, GNP-B and GNP-AB. Other linking moieties may also be used.

"Reporter substrate", "chemical substrate" and "substrate" are equivalent, and each refers to any molecule which is specifically recognized and modified by a catalytic nucleic acid molecule.

"Target" refers to a biological target, including, nucleic acid sequences (DNA and RNA), peptides, proteins, polysaccharides, fatty acids, toxins, phages, antibodies and so forth. The target of interest to be detected or measured by the instant invention, which comprises a sequence that hybridizes with a target domain, also referred to as sensor domain, of the catalytic nucleic acid molecule when contacted therewith in this method, and that can be either an entire molecule or a portion thereof.

In one embodiment, the present invention relates to a method of detecting a molecular target in a sample. The method may include: (a) contacting the sample with: (i) an un-catalyzed nucleic acid substrate, (ii) a catalytic nucleic acid, the catalytic nucleic acid configured for catalyzing the substrate solely in the presence of the target, and (iii) GNPs, the GNPs, which may be provided in a substantially dispersed form (for the purpose of this document, "substantially dispersed" includes "dispersed"), may be functionalized with a linking moiety for assembling with the un-catalyzed nucleic acid substrate; and (b) analyzing the sample to determine whether the GNPs remain substantially dispersed or are assembled with the un-catalyzed nucleic acid substrate, wherein the GNPs being in the substantially dispersed form is indicative that the target is present in the sample.

The GNPs may be functionalized with a nucleic acid strand A and/or a nucleic acid strand B. For example, 5'-thiol-modified Agg/A (Strand A) or 3'-thiol-modified Agg/B (Strand B) DNA. [34] A linker nucleic acid strand may include a substrate region for a catalytic nucleic acid molecule, and it may be designed to have its 5'-end complementary to 3' of Agg/A, and its 3'-end to complement 5' of Agg/B. The linker in its un-catalyzed form may then serve to cross-link GNPs through hybridization with strands A and B, forming GNP aggregate or assembled network. When the linker is cleaved, it may no longer serve to cross-link GNPs.

FIG. 1 illustrates an embodiment of an experimental setup. In FIG. 1B, two sets or populations of GNPs, GNP-A and GNP-B are functionalized with a nucleic acid strand A and strand B, respectively. However, as explained in the previous paragraph, one population of GNPs having strands A and B may be used. For example, 5'-thiol-modified Agg/A (Strand A) or 3'-thiol-modified Agg/B (Strand B) DNA, respectively. A linker nucleic acid strand may be designed to have its 5'-end complementary to 3' of Agg/A, and its 3'-end to complement 5' of Agg/B. The linker may serve to cross-link GNP-A and GNP-B through hybridization, forming GNP aggregate or assembled network (FIG. 1-B).

Close proximity of linked GNPs may cause coupling of their individual localized plasmon fields, leading to the shift in their peak absorbance to a longer wavelength, and solution color changes from red to purple. In addition, the linker strand may also include a substrate sequence that may be cleaved by a catalytic nucleic acid molecule, for example a multicomponent nucleic acid enzyme (MNAzyme), which is one of the reported DNA-responsive DNAzymes. MNAzyme uses $Mg^{2+}$ as the divalent cation, and has optimal activity at 50° C. Among the three reported DNA-responsive bipartite DNAzymes, the inventors chose to work with the MNAzyme, since it has the highest catalytic rate.[9,24,25, 29] In this document, MNAzymes are used as an example, however, it should be understood that other catalytic nucleic acid molecules, including other DNA-responsive DNAzymes, and DNAzymes that respond to metal ions, such as lead and uranyl, or small molecule targets, such as adenosine, FMN and ATP, may be used as well.[46-48]

As illustrated in FIG. 1 B, the catalytic nucleic acid molecule initially comprises of two inactive parts or precatalytic subunits, Part A and Part B. Each one of Part A and B may include a domain or arm complementary to at least a different portion of a target of interest (target or sensor domain) and an domain capable of interacting with at least a portion of a substrate to be cleaved (substrate domain). Initially in the inactive state, target's binding to the sensor domains bridges pre-catalytic subunits A and B, thereby bringing parts A and B together and forming the active catalytic structure, which can then hybridize to a substrate sequence and catalyze its cleavage (FIG. 1-A). [9] For MNAzymes, the substrate sequence may comprise DNA bases with two RNA nucleotides, which are required for cleavage, imbedded in the middle. [6]

The catalytic nucleic acid molecule may be made responsive to any biological target simply by changing the nucleotides of the sensor domains or sensor arms. The sequence of the substrate arms ensures specificity to a particular substrate, so that multiple MNAzyme-substrate pairs may be used in the same assay without cross-reactivity. Aptamers are nucleic acid molecules that bind with high specificity and sensitivity to biological targets. Aptamers may be created basically for any biological target [See U.S. Pat. No. 5,670,637]. The aptamer sequences may be incorporated in the sensor arm to bind any biological target of interest.

Referring to FIG. 1C, the sensing assay of the present invention may be implemented as a two-step system. In the first "amplification" step, a mix of catalytic nucleic acid molecules, such as MNAzymes, having a sensor domain for a desired target, and linkers (the MNAzyme substrate) may be added to a sample solution, which may be suspected of having the target of interest. The mix MNAzyme/linker may be buffered. The sample with the mix may be incubated at a suitable temperature and for a suitable time. The mix may be done under conditions suitable for permitting catalytic nucleic acid activity. The temperature and time of incubation of the mix may depend on the DNAzyme being used. If the target is present in the sample, the target may bind the sensor domains of the MNAzyme subunits and activate the MNAzymes. Each active MNAzyme may in turn catalyze cleavage of multiple linkers, which effectively translates into signal amplification. In a second "detection" step, a mix of GNP-A and GNP-B (or, alternatively GNP-AB) may be added to the sample solution. In the absence of the target intact linkers interact with the GNPs to form aggregate or assembled network, turning solution purple. In contrast, presence of a target results in linker degradation, the GNP-A and GNP-B (or GNP-AB) do not get cross-linked (i.e. remain in unassembled form), and the solution remains red. A more sensitive visual detection may be achieved by spotting the solution onto thin layer chromatography (TLC) plates. [31] TLC plates intensify the color differences allowing for a more sensitive visual detection, and may be stored for later viewing. A measurement of the UV-vis spectroscopic shift of peak absorbance may also be used for confirmation. [35]

For a given GNP concentration there may be enough linker concentration able to crosslink the GNPs sufficiently to cause visual aggregation. With such a linker/GNP ratio, even if a small proportion of linker strands get cleaved by the MNAzymes, this should have an effect on GNP cross-linking state and color of the solution. Therefore, minimizing the linker concentration may effectively maximize assay sensitivity. Optimization results are presented in FIG. 2-A. Assay setup matched the experimental condition of the MNAzyme1 assay, but lacked the genetic target to prevent $Linker_1$ degradation. As the amount of $Linker_1$ is increased from 0 to 100 nM, there is a sigmoidal shift in the peak absorbance, λPeak, from 527 nm to 546 nm, indicating increase in GNP aggregate size. The TLC spot color follows a similar, but steeper sigmoidal trend. The spots appear red up to 20 nM, then gradually shift to dark purple-black at 50 nM, and remain unchanged for higher concentrations. Based on both color change and peak shift we chose 40 nM as the optimal $Linker_1$ concentration.

Figure 2:
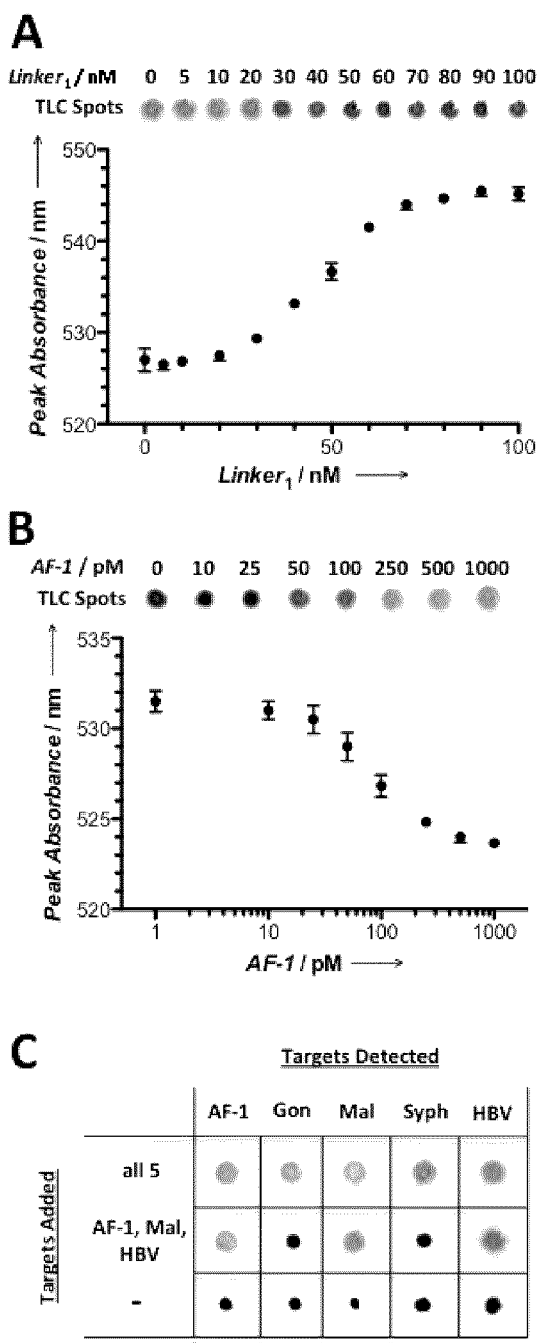
FIG. 2: Panel A—Optimization of Linker1 concentration. Panel B—Sensitivity of detecting AF-1 genetic target. For panels A and B—Top: colorimetric readout on TLC plate. Bottom: shift in the peak absorbance. Data based on 3 replicates; error bars are standard errors. Panel C—Parallel detection of 5 targets: AF-1, genetic sequences from *N. gonorrhoeae* (Gon) and *T. pallidum* (Syph) bacteria, malarial parasite *P. falciparum* (Mal), and HBV virus. Detection of all 5 targets (top row), 3 out of 5 targets (center row), or no-target control (bottom row). Spot color indicates target presence (large grey spots) or absence (small black spots). Images were adjusted for contrast and brightness.
Figure 3:
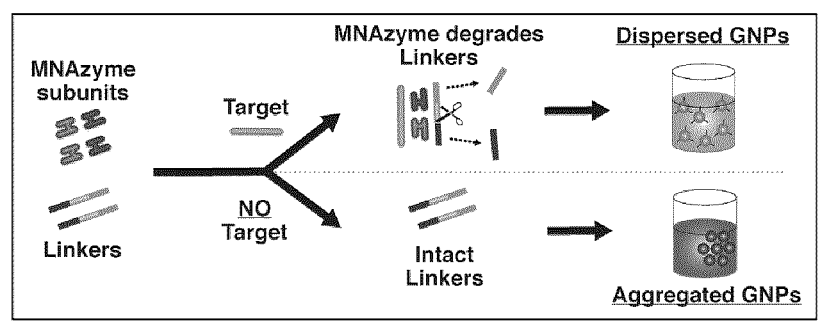
FIG. 3: Graph illustrating DNAzyme signal amplification combined with surface plasmon properties of gold nanoparticles to achieve colorimetric detection of biological targets in accordance to one embodiment of the present invention.

The MNAzyme assay outlined in FIG. 1 was carried out to detect AF-1 as the biological target (in this case a DNA target). As previously determined, the linker at 40 nM was used, and AF-1 was assayed from 0 pM to 1 nM (FIG. 2-B). Similar to FIG. 2-A, spectroscopic data demonstrates a sigmoidal, but decreasing trend in λPeak. Peak absorbance shifts from 533 nm for the sample without AF-1 to 523 nm for 1 nM of target. The color of TLC spots follows similar trend, remaining purple from 0 pM to 25 pM AF-1, then gradually shifting to reach red at 500 pM and 1000 pM. Both spectroscopic and spot color data establish the limit of detection of this assay at about 50 pM. This sensitivity is slightly lower than 5 pM reported for the fluorescence readout. [9]

Figure 4:
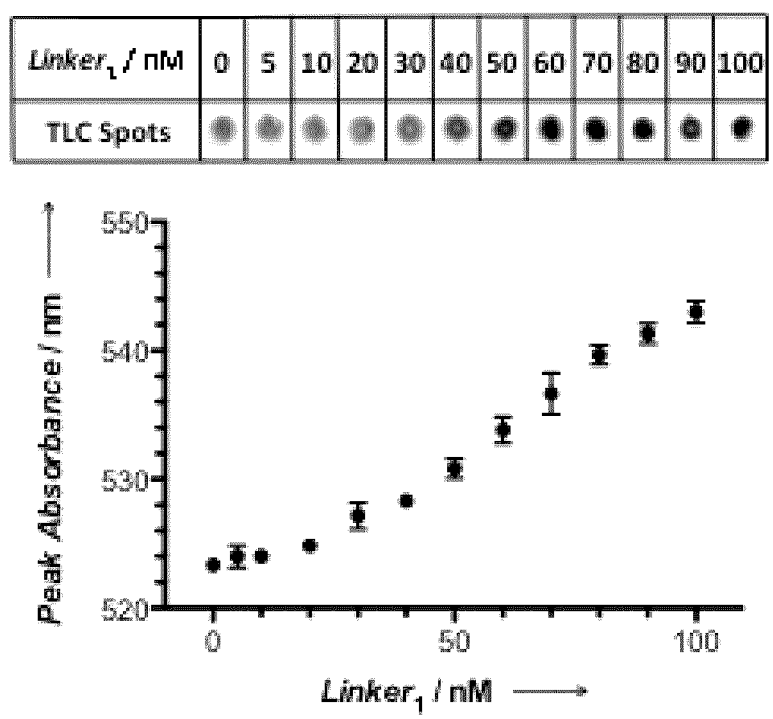
FIG. 4: Top: colorimetric readout on TLC plate. Bottom: shift in the SPR peak absorbance. Data based on 3 replicates; error bars are standard errors.

If the linker is chosen as the genetic detection target instead of AF-1, the experiment of FIG. 2-A matches the original MNAzyme-free direct DNA detection assay reported by Mirkin group (the inventors confirmed that the 50° C., 1 hour incubation step does not affect assay results, FIG. 4). [31] Based on FIG. 2-A, our implementation of this assay has detection sensitivity of ~30 nM. Therefore, inclusion of MNAzyme enzymatic signal amplification step increases detection sensitivity by a factor of 600.

The detection methods of the present invention may be used to detect a single target or to detect multiple targets in parallel (FIG. 1-D). The inventors tested with 4 additional targets corresponding to genetic sequences for gonorrhea (Gon)[36] and syphilis (Syph)[37] bacteria, malaria parasite (Mal),[38] and hepatitis B virus (HBV). [39] These infectious diseases are prevalent in both the developed and developing world, and can cause severe health problems and death in patients that are not properly diagnosed and treated. For example, to detect four targets, four MNAzyme-Linker-GNP sets may be developed, each specific for one of the targets. For example, for malaria, MNAzymeMal may include substrate arms specific for LinkerMal, and sensor arms complementary to Mal target, but not other linker sequences or targets. LinkerMal, in turn, could aggregate GNP-AMal and GNP-BMal, but not other GNP pairs. Likewise, MNAzymeGon for gonorrhea, MNAzymeHBV for hepatitis B, MNASyph for syphilis, and so forth.

In the first step of the assay, a solution suspected of containing more than one biological targets may be added to a reaction tube containing a mixture of different sets of MNAzymes/linker pairs, each set being specific for a target of interest. For example, if the targets of interest include AF-1, gonorrhea, syphilis, malaria and HBV, then 5 sets of MNAzyme-Linker pairs (MNAzymeAF-1, MNAzymeGon, MNAzymeSyph, MNAzymeMal and MNAzymeHBV) may be used. The mixture and the sample solution may then be incubated at a determined temperature and for a sufficient amount of time. Assuming AF-1 and Gon targets are present in the reaction tube, they activate MNAzymeAF-1 and MNAzymeGon, which in turn degrade LinkerAF-1 and LinkerGon. The other 3 linkers (i.e. LinkerSyph, LinkerMal and LinkerHBV) remain intact. In the second step, the MNAzyme-Linker-target solution is transferred to 5 detection tubes, each containing target-specific GNP pair. Any linkers that remain un-cleaved aggregate the corresponding GNP pairs, turning solution purple. In contrast, Linkers cleaved by target-activated MNAzymes are not able to cross-link associated GNP pairs, and solution remains red. In the example above, only mixtures in AF-1 and Con-specific detection tubes would remain red. Following this protocol all 5 targets were detected simultaneously (FIG. 2-C). In addition, the assay with lyophilized components was used to correctly identify AF-1, Mal and HBV sequences in sample mixture contained 3 out of 5 targets.

The present invention also provides for a kit for detecting a biological target of interest in a sample. In one embodiment, the kit may include: (a) an un-catalyzed nucleic acid substrate, (b) catalytic nucleic acid capable catalyzing the un-catalyzed substrate solely in the presence of the target, and (c) GNPs functionalized with a linking moiety to assemble with the un-catalyzed nucleic acid substrate. The GNPs may be provided substantially dispersed. The kit may include GNP-A and GNP-B or the kit may include GNP-AB. The kit may also include other ingredients that may be necessary for optimal activation of the catalytic nucleic acid molecule. The kit may also include a TLC. The ingredients (for example the linker, pre-catalytic subunits with or without the populations of GNPs) may be provided as a lyophilized mixture. In aspects of the invention, the kit may also include two or sets of un-catalyzed nucleic acid substrate, catalytic nucleic acid and GNPs that are target specific, that may be used in methods to simultaneously detect more than one target of interest in a sample.

In another embodiment, the present invention provides for lyophilization of assay components. In this form reagents remain functionally stable during storage and transport, making them well suited for POC testing. [40] The ingredients used in the methods of the present invention may conveniently be dehydrated or lyophilized for storage, transportation and extended shelf-life. For example, the catalytic nucleic acid molecules and the linkers may be lyophilized and provided as a freeze-dried mixture that may be added to a sample being tested. The GNPs may also be lyophilized and added to the freeze-dried mixture.

Advantages

DNAzyme-GNP assay of the present invention provides a simple and fast colorimetric scheme for detection of biological targets, including genetic targets of bacterial, viral and fungal origins with high sensitivity without the need for purification and separation steps. Results may be archived when spotted on TLC plates. To the knowledge of the applicants, this is the first report of combining the multi-component DNA-responsive DNAzyme with gold nanoparticle colorimetric platform.

The assay of the present invention may detect multiple genetic sequences in parallel and is easily translatable to new targets.

Color-based readout that does not require any complex equipment, and uses stable and cost-effective reagents make this experimental approach particularly suitable for POC testing. Furthermore, it is difficult to identify specific requirements for analytical sensitivity of a pathogen as this may vary based on the treatment strategy and whether one analyzing a single or co-infection.

Improved sensitivity may be achieved by modifying the nanoparticle size and chemistry, varying the length of MNAzyme/Linker or target sequences,[41] or by combining the fast catalytic rate of MNAzyme and colorimetric plasmonic readout with the sensitive protein-free autocatalytic DNAzyme approach demonstrated by the Willner group. [23, 42] Furthermore, in a complete point-of-care system, extra components may be added that can extract the genetic targets of interest. Such technologies have been developed for isolating targets from blood and stool samples. [43-45]

Freeze-drying of the components used in the methods of the present invention, provides storage, transportation and shelf-life advantages, not seen and not possible in DNAzyme methods of the prior art.

In order to aid in the understanding and preparation of the present invention, the following illustrative, non-limiting examples are provided.

EXAMPLES

Materials

HAuCl4, sodium citrate tribasic, sodium phosphate monobasic, sodium phosphate dibasic, magnesium chloride and potassium chloride were purchased from Sigma-Aldrich. Sodium chloride, Tween-20 and Tris were purchased from BioShop (Burlington, ON, Canada). Hydrochloric acid and nitric acid were purchased from Caledon Laboratories (Georgetown, ON, Canada). Thiolatedmethoxyl polyethylene glycol MW=1000 Da (mPEG-SH$_{1000}$) was purchased from Laysan BIO (Arab, Ala.). RPSF reversed phase hydrocarbon impregnated silica gel TLC plates were purchased from Analtech (Newark, Del.). All RNA-containing Linker DNA strands were purchased from Integrated DNA Technologies (IDT) in HPLC-purified lyophilized form. All other DNA sequences were purchased from BioBasic (Markham, ON, Canada) and purified (thiol-functionalized sequences were purified by HPLC and non-functionalized ones by HAP purification) and lyophilized by the company. All lyophilized DNA sequences were re-suspended in UltraPure distilled water (Invitrogen) to 100 μM concentration and stored at −20° C. DNA sequences used in the study are outlined in Table 1.

TABLE 1

List of DNA sequences

| NAME | SEQ ID | SEQUENCE (5'-to-3') | NOTES |
|---|---|---|---|
| 1. GNP-immobilized Agg sequences for GNP-A and GNP-B | | | |
| Agg$_1$/A$^a$ | 1 | HS-*AAAAAAAAAA* CCT ATC GAC CAT GCT | For all Agg sequences underlined region binds appropriate Linker strand, 10 bp poly-A spacer is *italicized* |
| Agg$_{Gon}$/A$^b$ | 2 | HS-*AAAAAAAAAA*TAA CAA TAA TCC CTC | |
| Agg$_{Mal}$/A$^c$ | 3 | HS-*AAAAAAAAAA* ATG GCC GAT GTA TGT | |
| Agg$_{Syph}$/A$^c$ | 4 | HS-*AAAAAAAAAA*CGA GTG AGT GCG ACG | |
| Agg$_{HBV}$/A$^c$ | 5 | HS-*AAAAAAAAAA*TTA TTG GTG TTA CTC | |
| Agg$_1$/B$^a$ | 6 | GCG CTA GAG TCG TTT*AAAAAAAAAA*-SH | |
| Agg$_{Gon}$/B$^b$ | 7 | ATC CTT ATC AAT ATT*AAAAAAAAAA*-SH | |
| Agg$_{Mal}$/B$^c$ | 8 | AGA GGA AAG TAG GCT*AAAAAAAAAA*-SH | |
| Agg$_{Syph}$/B$^c$ | 9 | GGT GGC TTA CAG TCA*AAAAAAAAAA*-SH | |
| Agg$_{HBV}$/B$^c$ | 10 | TGT AGG GCA TGT AGT*AAAAAAAAAA*-SH | |
| 2. Linkers | | | |
| Linker$_1$$^d$ | 11 | AGC ATG GTC GAT AGG T<u>AA</u> GGT TTC CTC <u>rGrU CCC TGG GCA</u> TAA ACG ACT CTA GCG C | For all Linkers, Mz binds and cleaves (between imbedded RNA rG-rU) underlined region, *italicized* region binds Agg strand A, and bolded region binds Agg strand B. |
| Linker$_{Gon}$$^d$ | 12 | G AGG GAT TAT TGT TAT <u>ACT CAC TAT</u> <u>rGrU</u> GGA AGA GAT GTA ATA TTG ATA AGG AT | |
| Linker$_{Mal}$$^e$ | 13 | ACA TAC ATC GGC CAT TCG <u>CAA ACC ATA</u> <u>rGrU GAG AAC ACG</u> AGC CTA CTT TCC TCT | |
| Linker$_{Syph}$$^f$ | 14 | CGT CGC ACT CAC TCGTTG <u>TGA CAC TAT</u> <u>rGrU AGC GAT CTT</u> GTT GAC TGT AAG CCA CC | |
| Linker$_{HBV}$$^g$ | 15 | GAG TAA CAC CAA TAATTG <u>CTG GAC AGA</u> <u>rGrU GTA TAG GAT TTA</u> CTA CAT GCC CTA CA | |

TABLE 1-continued

List of DNA sequences

| NAME | SEQ ID | SEQUENCE (5'-to-3') | NOTES |
|---|---|---|---|

3. MNAzyme subunits A and B

| NAME | SEQ ID | SEQUENCE (5'-to-3') | NOTES |
|---|---|---|---|
| $Mz_1/A^h$ | 16 | AGC TGC TGC CCG TGC TGG TGA CAA CGA GAG GAA ACC TT | For all MNAzyme (Mz) sequences, bolded region binds the target DNA and *italicized* region binds the appropriate Linker sequence. Underlined region forms half of the catalytic core. |
| $Mz_{Gon}/A^i$ | 17 | TGC CAA TAT CGG CGG CCG ATG ACA ACG *AAT AGT GAG T* | |
| $Mz_{Mal}/A^i$ | 18 | AAC TCA ATC ATG ACT ACC CGA CAA CGA *TAT GGT TTG CG* | |
| $Mz_{Syph}/A^i$ | 19 | GTC CAT CGG CAA ACA CGT CAA CAA CGA *ATA GTG TCA CA* | |
| $Mz_{HBV}/A^i$ | 20 | CAG GAG GTT GGT GAG TGA TTA CAA CGA *TCT GTC CAG CA* | |
| $Mz_1/B^h$ | 21 | *TGC CCA GGG AGG* CTA GCT CCA TTG CCC CAT GTG AAG TCA | |
| $Mz_{Gon}/B^i$ | 22 | *CAT CTC TTC CAG* GCT AGC TAC GGT ACC TGA AGA ATA AGC | |
| $Mz_{Mal}/B^i$ | 23 | *CAC GTG TTC TCA* GGC TAG CTT CTG TTA TGA ACA CTT AAT TTT | |
| $Mz_{Syph}/B^i$ | 24 | *CAA GAT CGC TAG* GCT AGC TAC TGC AGC ATC CAT CAG AGT CT | |
| $Mz_{HBV}/B^i$ | 25 | *AAT CCT ATA CAG* GCT AGC TGG AGG TTG GGG ACT GCG AAT TT | |

4. Target sequences

| NAME | SEQ ID | SEQUENCE (5'-to-3') | NOTES |
|---|---|---|---|
| AF-1$^j$ | 26 | CAG TGA CTT CAC ATG GGG CAA TGGCAC CAG CAC GGG CAG CAG CTG GC | For all target sequences, bolded region is bound by the appropriate Mz part A, and underlined region is bound by Mz part B. |
| Gon$^k$ | 27 | TGC TTA TTC TTC AGG TAC CGTCAT CGG CCG CCG ATA TTG GCA AC | |
| Mal$^l$ | 28 | AAA ATT AAG TGT TCA TAA CAG ACG GGT AGT CAT GAT TGA GTT CAT TGT GT | |
| Syph$^l$ | 29 | GGA GAC TCT GAT GGA TGC TGC AGTTGA CGT GTT TGC CGA TGG ACA G | |
| HBV$^l$ | 30 | GCC AAA ATT CGC AGT CCC CAA CCT CCA ATC ACT CAC CAA CCT CCT GTC CTC CAA | |

$^a$sequences adapted from (1).
$^b$sequences adapted from (2).
$^c$sequences were randomly generated.
$^d$MNAzyme-cleavable sequences (underlined) adapted from (3).
$^e$MNAzyme-cleavable sequences (underlined) adapted from (4).
$^f$MNAzyme-cleavable sequences (underlined) adapted from (5).
$^g$MNAzyme-cleavable sequences (underlined) adapted from (6).
$^h$Mz$_1$ subunit sequences taken from (3).
$^i$Mz$_1$ catalytic core sequence (underlined) used for all Mz. Linker and target binding sequences adjusted to match corresponding Linker/target sequences.
$^j$sequence taken from (3).
$^k$sequence designed to target 16 S ribosomal RNA gene from *Neisseria gonorrhoeae* (7).
$^l$sequences were chosen based on: Mal: (8), Syph: (9), and HBV: (10). Specifically, the authors indicated the PCR primers that they used for detection of the microorganisms by PCR method. We obtained the microorganisms' genomic DNA from GenBank (Mal: 16S ribosomal RNA not in asexual parasites, GenBank accession M19173; Syph: *Treponema pallidum* subsp. *pallidum* str. Nichols chromosome, complete genome, GenBank accession NC_000919, HBV: Hepatitis B virus isolate RS1, complete genome, GenBank accession HQ236014) and identified the specific regions that these PCR primers would amplify. The DINAMelt Web Server Two-state melting was used to identify the 46-54 base pair long regions within these amplicons containing the least amount of secondary structure [Markham, N. R. & Zuker, M. (2005) DINAMelt web server for nucleic acid melting prediction. Nucleic Acids Res., 33, W577-W581; the server can be found at mfold.rna.albany.edu/?q=DINAMelt/Two-state-folding]. These regions were chosen as MNAzyme targets.

Instrumentation:

Spectroscopic measurements were performed using a SHIMADZU UV-Visible spectrophotometer UV-1601PC (Kyoto, Japan). DLS measurements were performed on MALVERN Nano-ZS Zetasizer (Worcestershire, UK). Freeze drying was performed in LABCONCO (Kansas City, Mo.) LYPH-LOCK 6 Freeze Dry System. TLC spots were photographed with Canon PowerShot S95 camera.

Experimental Details:

Preparation of 13 nm Gold Nanoparticles (GNPs):

1 mL of 25 nM HAuCl$_4$ was added to 98 mL of nanopure water in 250 mL flask prewashed with 100 mL of aqua regia (3 parts hydrochloric acid, 1 part nitric acid)(11). After bringing solution to a rapid boil, stirring was initiated on a benchtop stir plate, and 1 mL of 33 mg/mL of sodium citrate tribasic was added. The mixture was incubated for 10 min under boiling and stirring conditions (at which point solution color turned red), and then cooled to room temperature. DLS measurement was used to verify nanoparticles size and monodispersity (only particles with polydispersity index <0.1 were used). Tween-20 was then added to a final concentration of 0.01% v/v and GNPs were concentrated by 1× centrifugation at 12,000 g for 30 minutes. GNP concentration was measured by UV-vis spectroscopy by using absorbance at Δ=520 nm (assuming extinction coefficient of $2.33 \times 10^8$ M$^{-1}$ cm$^{-1}$ and GNP diameter of 13 nm), then adjusted to 100 nM using nanopure water with 0.01% v/v Tween-20. The extinction coefficient for gold was calculated using the formula from (12). There was a small error in the published version; the corrected formula is as follows:

Extinction coefficient=
$10^{(1.0643 * LOG\, [3/2 * 3.141592654 * (diameter)^3] + 4.0935)}$ Adsorbing Thiolated AggDNA onto GNPs We followed a protocol described previously by Mirkin group (13) with a few modifications. 60 μL of 100 nM 13 nm GNPs (final concentration 10 nM) were mixed with 60 μL of 32 μM of one of thiol-functionalized Agg strands (final concentration 3.2 μM, or 320 Agg/GNP) in 600 μL of 10 mM phosphate buffer (PB, pH 7.2) with 0.01% v/v Tween-20. Solution was incubated at room temperature for 20 minutes. 3.43 M NaCl solution in 10 mM PB with 0.01% v/v Tween-20 was then added to the reaction mixture in 10 steps according to the schedule of Table 2 to reach final concentration of 0.88M NaCl. Between each addition step and after the last addition step the mixture was incubated for 20 minutes at room temperature. Salt is required to block the negative charges on DNA molecules to allow high density loading of DNA on GNP surface; slow aging process is used to prevent salt-induced aggregation of GNPs. Next, 30 μL of 2 mM mPEG-SH$_{1000}$ were added (10,000 mPEG-SH$_{1000}$ molecules per GNP), and reaction mixture was incubated for 30 min at 60° C. mPEG-SH$_{1000}$ adsorption step was included to block any DNA-free areas on GNP surface, thus improving the stability of DNA-functionalized GNPs against aggregation in salts during the MNAzyme 50° C. cleavage step (see below), centrifugation, and storage. Finally, DNA-functionalized GNPs were purified by 3× centrifugation at 16,000 g for 30 min, resuspended in nanopure water with 0.01% v/v Tween-20 at 11 nM concentration, and stored at 4° C.

TABLE 2

Salt addition schedule for loading thiolated AggDNA onto 13 nm GNPs

| STEP | Reaction* Volume (μL) | Volume of Salt Mix** Added (μL) | Final [NaCl] (M) |
|---|---|---|---|
| 1 | 600.00 | 18.02 | 0.10 |
| 2 | 618.02 | 18.56 | 0.20 |
| 3 | 636.58 | 19.12 | 0.29 |
| 4 | 655.69 | 19.69 | 0.38 |
| 5 | 675.38 | 20.28 | 0.47 |
| 6 | 695.67 | 20.89 | 0.56 |
| 7 | 716.56 | 21.52 | 0.64 |
| 8 | 738.07 | 22.16 | 0.72 |
| 9 | 760.24 | 22.83 | 0.80 |
| 10 | 783.07 | 23.52 | 0.88 |

*Initial reaction volume contains 10 nM of 13 nm GNPs and 3.2 μM of Agg DNA in 10 mM PB with 0.01% v/v Tween-20.
**Salt Mix contains 3.43M NaCl in 10 mM PB with 0.01% v/v Tween-20.

Optimizing Linker$_1$ Concentration (FIG. 2A)

Twelve 0.6 mL tubes were set up, each containing 2 μL of nanopure water, 2 μL of 10× MNAzyme buffer (0.1 M Tris-HCl, 0.5 M KCl, pH 8.3), 2 μL of 200 mM MgCl$_2$, and 2 μL of 2 μM [Mz$_1$/A+Mz$_1$/B] solution. In addition, each tube contained 2 μL of one of 50, 100, 200, 300, 400, 500, 600, 700, 800, 900, or 1000 nM of Linker$_1$. The 12$^{th}$ tube was included as negative control and contained 2 μL of nanopure water instead of Linker$_1$. The tubes were incubated at 50° C. for 1 hour to mimic MNAzyme cleaving step. To each tube 5 μL of 11 nM GNP$_1$-A (13 nm GNPs functionalized with Agg$_1$/A DNA) and 5 μL of 11 nM GNP$_1$-B (13 nm GNPs functionalized with Agg$_1$/B DNA) were added. The samples (20 μL final volume) were incubated at 50° C. for 20 minutes, then cooled to room temperature for 5 minutes to allow GNPs to be cross-linked by Linker$_1$. 3 μL of the mixture were then spotted on TLC plates to visualize the degree of aggregation. Remaining mixture was used to measure the location of the surface plasmon resonance (SPR) absorbance peak. This experiment was performed in triplicate.

Referring to FIG. 4, the assay experimentally matches the experiment described in FIG. 2A, with the exception that in this case the samples were not incubated for 1 hr at 50° C. before colorimetric detection. Similar to FIG. 2A, the sensitivity of Linker$_1$ detection is ~30 nM. This experiment was performed to confirm that inclusion of 1 hr/50° C. incubation step does not affect the sensitivity of the MNAzyme-free direct detection assay. Photographs of TLC spots were adjusted for contrast and brightness (differences in spot color could be easily distinguished by a naked eye).

Determining MNAzyme Colorimetric Assay Sensitivity for Detection of AF-1 Genetic Target (FIG. 2B)

Eight 0.6 mL tubes were set up, each containing 2 μL of 10× MNAzyme buffer, 2 μL of 150 mM MgCl$_2$, 2 μL of 2 μM [Mz$_1$/A+Mz$_1$/B] solution, and 2 μL of 400 nM Linker$_1$. In addition, each tube contained 2 μL of one of 100, 250, 500, 1000, 2500, 5000, or 10000 μM of AF-1. The 8$^{th}$ tube was included as negative control and contained 2 μL of nanopure water instead of AF-1. The samples were incubated for 1 hour at 50° C. to allow AF-1-activated MNAzymes to cleave Linker$_1$. To each tube 5 μL of 11 nM GNP$_1$-A and 5 μL of 11 nM GNP$_1$-B were then added (20 μL final volume), and the samples were incubated at 50° C. for 20 minutes followed by cooling to room temperature for 5 minutes. 3 μL of the mixture were then spotted on TLC plates to visualize the degree of aggregation. Remaining mixture was used to measure the location of the SPR absorbance peak. This experiment was performed in triplicate.

Detecting Multiple DNA Targets in Parallel (FIG. 2C)

MNAzyme mix was made by mixing 100 μL of each of the following: 2 μM [Mz$_1$/A+Mz$_1$/B], 2 μM [Mz$_{Gon}$/A+Mz$_{Gon}$/B], 2 μM [Mz$_{Mal}$/A+Mz$_{Mal}$/B], 2 μM [Mz$_{Syph}$/A+Mz$_{Syph}$/B], and 2 μM [Mz$_{HBV}$/A+Mz$_{HBV}$/B] solutions. Linker mix was made by mixing 100 μL of each of: 2 μM Linker$_1$, 2 μM Linker$_{Gon}$, 2 μM Linker$_{Mal}$, 2 μM Linker$_{Syph}$, and 2 μM Linker$_{HBV}$. To detect all 5 target sequences in parallel, two solutions were set up in 0.6 mL tubes, each containing 10 μL of 10× MNAzyme buffer, 10 μL of 400 mM MgCl$_2$, 10 μL of MNAzme mix, 40 μL of Linker mix, and 20 μL of nanopure water. To the first reaction solution, 2 μL each of 1 μM AF-1, 1 μM Gon, 1 μM$_{Mal}$, 1 μM Syph, and 1 μM HBV targets were added. In contrast, 10 μL of nanopure water were added to the second solution, which was used as a negative control solution. In addition, 5 detection mixes were set up in 0.6 mL tubes in duplicate, each containing one of the following GNP pairs: (i) [5 μL of 11 nM GNP$_1$-A and 5 μL of 11 nM GNP$_1$-B], or (ii) [5 μL of 11 nM GNP$_{Mal}$-A and 5 μL of 11 nMGNP$_{Mal}$-B], or (iii) [5 μL of 11 nM GNP$_{Gon}$-A and 5 μL of 11 nM GNP$_{Gon}$-B], or (iv) [5 μL of 11 nM GNP$_{Syph}$-A and 5 μL of 11 nM GNP$_{Syph}$-B], or (v) [5 μL of 11 nM GNP$_{HBV}$-A and 5 μL of 11 nM GNP$_{HBV}$-B]. The reaction and control solutions were incubated for 1 hour at 50° C. to allow activated MNAzymes to cleave their corresponding linkers. 10 μL from reaction solution were then transferred to the 5 tubes of the first detection mix set, and 10 μL from control solution to the 2$^{nd}$ 5 detection mix tubes. All samples were incubated for 20 minutes at 50° C., then for 5 minutes at room temperature to allow GNP aggregate formation. 3 μL from each tube were spotted on TLC plates for color readout.

The scheme for detecting 3 (AF-1, Mal, and HBV) out of 5 possible targets in parallel included lyophilization of the components. Reaction solution was premade by mixing 6 μL of 10× MNAzyme buffer, 6 μL of 400 mM MgCl$_2$, 6 μL of MNAzyme mix, 24 μL of Linker mix, and 12 μL of nanopure water in 1.5 mL tube. In addition, 5 GNP-containing detection mix tubes were set up as described above. All of the samples were frozen at −80° C. for 30 minutes, freeze-dried overnight, and stored at room temperature. On the day of the experiment, lyophilized reaction solution was resuspended in 54 μL of nanopure water, and 1.2 μL of 2 μM AF-1, 1.2 μL of 2 μM Mal, 1.2 μL of 2 μM HBV targets and 2.4 MI of nanopure water were added. The reaction solution was then incubated for 1 hour at 50° C. Next, 10 μL of the solution was transferred to each lyophilized detection mix, and the detection tubes were incubated for 20 minutes at 50° C. and cooled to room temperature for 5 minutes. 3 μL from each tube were spotted on TLC plates for readout.

As many changes can be made to the embodiments described above without departing from the scope of the invention, it is intended that all material contained herein be interpreted as illustrative of the invention and not in a limiting sense.

The documents referenced within the preceding description are as follows:

REFERENCES

All documents referred to in this document, are incorporated herein by reference.

Documents Referred to in the Description

[1] S. Binder, A. M. Levitt, J. J. Sacks, J. M. Hughes, *Science* 1999, 284, 1311-1313.
[2] T. S. Hauck, S. Gin, Y. Gao, W. C. W. Chan, *Adv. Drug Delivery Rev.* 2010, 62, 438-448.
[3] J. Weile, C. Knabbe, *Anal. Bioanal. Chem.* 2009, 394, 731-742.
[4] M. J. Espy, J. R. Uhl, L. M. Sloan, S. P. Buckwalter, M. F. Jones, E. A. Vetter, J. D. C. Yao, N. L. Wengenack, J. E. Rosenblatt, F. R. Cockerill III, T. F. Smith, *Clin. Microbiol. Rev.* 2006, 19, 165-256.
[5] S. Gin, E. A. Sykes, T. L. Jennings, W. C. W. Chan, *ACS Nano* 2011, 5, 1580-1587.
[6] K. Schlosser, Y. Li, *ChemBioChem* 2010, 11, 866-879.
[7] S. W. Santoro, G. F. Joyce, *Proc. Natl. Acad. Sci. U.S.A.* 1997, 94, 4262-4266.
[8] R. R. Breaker, G. F. Joyce, *Chemistry & biology* 1994, 1, 223-229.
[9] E. Mokany, S. M. Bone, P. E. Young, T. B. Doan, A. V. Todd, *J. Am. Chem. Soc.* 2010, 132, 1051-1059.
[10] W. Zhao, J. C. F. Lam, W. Chiuman, M. A. Brook, Y. Li, *Small* 2008, 4, 810-816.
[11] J. Liu, Y. Lu, *J. Am. Chem. Soc.* 2004, 126, 12298-12305.
[12] J. Liu, Y. Lu, *J. Am. Chem. Soc.* 2003, 125, 6642-6643.
[13] J. Liu, Y. Lu, *Org. Biomol. Chem.* 2006, 4, 3435-3441.
[14] D. Mazumdar, J. Liu, G. Lu, J. Zhou, Y. Lu, *Chem. Commun.* 2010, 46, 1416.
[15] X. Miao, L. Ling, X. Shuai, *Chem. Commun.* 2011, 47, 4192.
[16] H. Wei, B. Li, J. Li, S. Dong, E. Wang, *Nanotechnology* 2008, 19, 095501.
[17] J. H. Lee, Z. Wang, J. Liu, Y. Lu, *J. Am. Chem. Soc.* 2008, 130, 14217-14226.
[18] Z. Wang, J. H. Lee, Y. Lu, *Adv. Mater.* 2008, 20, 3263-3267.
[19] J. Li, Y. Lu, *J. Am. Chem. Soc.* 2000, 122, 10466-10467.
[20] J. Liu, Y. Lu, *Anal. Chem.* 2004, 76, 1627-1632.
[21] J. Liu, Y. Lu, *J Fluoresc* 2004, 14, 343-354.
[22] D. Wang, B. Lai, D. Sen, *J. Mol. Biol.* 2002, 318, 33-43.
[23] F. Wang, J. Elbaz, R. Orbach, N. Magen, I. Willner, *J. Am. Chem. Soc.* 2011, 133, 17149-17151.
[24] F. Wang, J. Elbaz, C. Teller, I. Willner, *Angew. Chem. Int. Ed.* 2010, 50, 295-299.
[25] Y. V. Gerasimova, E. Cornett, D. M. Kolpashchikov, *ChemBioChem* 2010, 11, 811-817.
[26] S. Sando, A. Narita, T. Sasaki, Y. Aoyama, *Org. Biomol. Chem.* 2005, 3, 1002-1007.
[27] S. Sando, T. Sasaki, K. Kanatani, Y. Aoyama, *J. Am. Chem. Soc.* 2003, 125, 15720-15721.
[28] J. Kosman, B. Juskowiak, *Anal. Chim. Acta* 2011, 707, 7-17.
[29] D. M. Kolpashchikov, *ChemBioChem* 2007, 8, 2039-2042.
[30] M. Quinten, U. Kreibig, D. Schönauer, L. Genzel, *Surf. Sci.* 1985, 156, 741-750.
[31] R. Elghanian, J. J. Storhoff, R. C. Mucic, R. L. Letsinger, C. A. Mirkin, *Science* 1997, 277, 1078-1081.
[32] C. D. Medley, J. E. Smith, Z. Tang, Y. Wu, S. Bamrungsap, W. Tan, *Anal. Chem.* 2008, 80, 1067-1072.
[33] K. Sato, K. Hosokawa, M. Maeda, *Nucleic Acids Res.* 2005, 33, 1, e4.
[34] S. J. Hurst, A. K. R. Lytton-Jean, C. A. Mirkin, *Anal. Chem.* 2006, 78, 8313-8318.
[35] J. J. Storhoff, R. Elghanian, R. C. Mucic, C. A. Mirkin, R. L. Letsinger, *J. Am. Chem. Soc.* 1998, 120, 1959-1964.
[36] R. Rossau, L. Heyndrickx, H. Van Heuverswyn, *Nucleic Acids Res.* 1988, 16, 6227.
[37] J. Burstain, E. Grimprel, S. Lukehart, M. Norgard, J. Radolf, *J. Clin. Microbiol.* 1991, 29, 62-69.
[38] A. R. Bharti, K. P. Patra, R. Chuquiyauri, M. Kosek, R. H. Gilman, A. Llanos-Cuentas, J. M. Vinetz, *Am. J. Trop. Med. Hyg.* 2007, 77, 444-446.
[39] D. Paraskevis, A. Beloukas, C. Haida, A. Katsoulidou, Z. Moschidis, H. Hatzitheodorou, A. Varaklioti, V. Sypsa, A. Hatzakis, *Virol. J.* 2010, 7, 57.
[40] W. Abdelwahed, G. Degobert, S. Stainmesse, H. Fessi, *Adv. Drug Delivery Rev.* 2006, 58, 1688-1713.
[41] Y. Gao, W. L. Stanford, W. C. W. Chan, *Small* 2011, 7, 137-146.
[42] S. Shimron, F. Wang, R. Orbach, I. Willner, *Anal. Chem.* 2012, 84, 1042-1048.
[43] S. R. Jangam, D. H. Yamada, S. M. McFall, D. M. Kelso, *J. Clin. Microbiol.* 2009, 47, 2363-2368.
[44] A. V. Govindarajan, S. Ramachandran, G. D. Vigil, P. Yager, K. F. Boehringer, *Lab Chip* 2012, 12, 174-181.
[45] A. G. Freifeld, K. A. Simonsen, C. S. Booth, X. Zhao, S. E. Whitney, T. Karre, P. C. Iwen, H. J. Viljoen, *The Journal of Molecular Diagnostics* 2012, 14, 274-279.
[46] Liu, J.; Lu, Y. *J. Fluoresc.* 2004, 14, 343-354.
[47] Wang, D.; Lai, B.; Sen, D. *J. Mol. Biol.* 2002, 318, 33-43.
[48] Lee, J. H.; Wang, Z.; Liu, J.; Lu, Y. *J. Am. Chem. Soc.* 2008, 130, 14217-14226.

Documents Referred to in the Examples (1) Elghanian, R. Selective Colorimetric Detection of Polynucleotides Based on the Distance-Dependent Optical Properties of Gold Nanoparticles. *Science* 1997, 277, 1078-1081.
(2) Jin, R.; Wu, G.; Li, Z.; Mirkin, C. A.; Schatz, G. C. What Controls the Melting Properties of DNA-Linked Gold Nanoparticle Assemblies? *J. Am. Chem. Soc.* 2003, 125, 1643-1654.
(3) Mokany, E.; Bone, S. M.; Young, P. E.; Doan, T. B.; Todd, A. V. MNAzymes, a Versatile New Class of Nucleic Acid Enzymes That Can Function as Biosensors and Molecular Switches. *J. Am. Chem. Soc.* 2010, 132, 1051-1059.
(4) Zhao, W.; Lam, J. C. F.; Chiuman, W.; Brook, M. A.; Li, Y. Enzymatic Cleavage of Nucleic Acids on Gold Nanoparticles: A Generic Platform for Facile Colorimetric Biosensors. *Small* 2008, 4, 810-816.
(5) Liu, J.; Lu, Y. Design of asymmetric DNAzymes for dynamic control of nanoparticle aggregation states in response to chemical stimuli. *Org. Biomol. Chem.* 2006, 4, 3435.
(6) Wang, F.; Elbaz, J.; Teller, C.; Willner, I. Amplified Detection of DNA through an Autocatalytic and Catabolic DNAzyme-Mediated Process. *Angewandte Chemie International Edition* 2010, 50, 295-299.
(7) Rossau, R.; Heyndrickx, L.; Van Heuverswyn, H. Nucleotide sequence of a 16S ribosomal RNA gene from *Neisseria gonorrhoeae*. *Nucleic Acids Res* 1988, 16, 6227.
(8) R-Bharti, A.; Patra, K. P.; Chuquiyauri, R.; Kosek, M.; Gilman, R. H.; Llanos-Cuentas, A.; Vinetz, J. M. Short report: Polymerase chain reaction detection of *Plasmodium vivax* and *Plasmodium falciparum* DNA from stored serum samples: Implications for retrospective diagnosis of malaria. *American Journal of Tropical Medicine and Hygiene* 2007, 77, 444-446.
(9) Burstain, J.; Grimprel, E.; Lukehart, S.; Norgard, M.; Radolf, J. Sensitive Detection of *Treponema-Pallidum* by Using the Polymerase Chain-Reaction. *J Clin Microbiol* 1991, 29, 62-69.
(10) Paraskevis, D.; Beloukas, A.; Haida, C.; Katsoulidou, A.; Moschidis, Z.; Hatzitheodorou, H.; Varaklioti, A.; Sypsa, V.; Hatzakis, A. Development of a new ultra sensitive real-time PCR assay (ultra sensitive RTQ-PCR) for the quantification of HBV-DNA. *Virology journal* 2010, 7, 57.
(11) Perrault, S. D.; Walkey, C.; Jennings, T.; Fischer, H. C.; Chan, W. C. W. Mediating Tumor Targeting Efficiency of Nanoparticles Through Design. *Nano Lett.* 2009, 9, 1909-1915.
(12) Perrault, S. D.; Chan, W. C. W. Synthesis and Surface Modification of Highly Monodispersed, Spherical Gold Nanoparticles of 50-200 nm. *J. Am. Chem. Soc.* 2009, 131, 17042.
(13) Hurst, S. J.; Lytton-Jean, A. K. R.; Mirkin, C. A. Maximizing DNA Loading on a Range of Gold Nanoparticle Sizes. *Anal. Chem.* 2006, 78, 8313-8318.

Therefore what is claimed is:

1. A method of simultaneously detecting a presence or an absence of more than one different nucleic acid targets of interest in a sample, characterized in that the method comprises:
   (a) mixing the sample suspected of having the more than one different nucleic acid targets with target-specific sets of (i) target-specific un-catalyzed nucleic acid substrates and (ii) target-specific pre-catalytic nucleic acid subunits, each target-specific pre-catalytic nucleic acid subunit including a sensor domain for specifically hybridizing to one of the more than one different nucleic acid targets, and a catalytic domain configured for catalyzing its corresponding target-specific un-catalyzed nucleic acid substrate solely when the corresponding specific target is bound to the sensor domain;
   (b) contacting the mixture of step (a) with separate target-specific populations of gold nanoparticles (GNPs), the GNPs in each target-specific population functionalized with a linking moiety for assembling with its corresponding target-specific un-catalyzed nucleic acid substrate and molecules of polyethylene glycol; and
   (c) optically determining for each separate target-specific population of GNPs whether the target-specific GNPs are in an assembled form with the corresponding target specific un-catalyzed nucleic acid substrate or in a substantially dispersed form, wherein in the assembled form the GNPs turn the sample to a first color, and in the substantially dispersed form the GNPs turn the sample to a second color thereby simultaneously detecting the presence or absence of the more than one different nucleic acid targets of interest in the sample.

2. The method of claim 1, characterized in that said method further includes spotting the sample onto thin layer chromatography (TLC) plates for visual detection.

3. The method of claim 2, characterized in that the method further includes storing the TLC plates for later viewing.

4. The method of claim 1, characterized in that the method further comprises a spectroscopic measurement of the UV-visible spectroscopic shift of peak absorbance.

5. The method of claim 1, characterized in that the target specific pre-catalytic nucleic acid subunits and the target-specific un-catalyzed nucleic acid substrate are provided as a lyophilized mixture.

6. The method of claim 1, characterized in that the target specific pre-catalytic nucleic acid subunits, the target-specific un-catalyzed nucleic acid substrate and the GNPs are provided lyophilized.

7. The method of claim 1, characterized in that the linking moiety includes nucleic acid strands that hybridize with a 3' end and a 5' end of the corresponding target specific un-catalyzed nucleic acid substrate for assembling.

8. A kit for detecting a presence or an absence of more than one different nucleic acid targets of interest in a sample, characterized in that the kit comprises: (a) target-specific un-catalyzed nucleic acid substrates and (b) target-specific pre-catalytic nucleic acid subunits, each target-specific pre-catalytic nucleic acid subunit including a sensor domain for specifically hybridizing to one of the more than one different nucleic acid targets, and a catalytic domain configured for catalyzing its corresponding target-specific un-catalyzed nucleic acid substrate solely when the corresponding specific target is bound to the sensor domain;
   and (c) separate target-specific populations of gold nanoparticles (GNPs), the GNPs in each target-specific population functionalized with a linking moiety for assembling with its corresponding target-specific un-catalyzed nucleic acid substrate and molecules of polyethylene glycol; characterized in that the kit is configured to perform the method of claim 1.

9. The kit of claim 8, characterized in that the GNPs assembled with the target-specific un-catalyzed nucleic acid substrate turn the sample to a first color, and GNPs in a substantially dispersed form turn the sample to a second color.

10. The kit of claim 8, characterized in that the target specific un-catalyzed nucleic acid substrate and the target-specific pre-catalytic nucleic acid subunits are in a lyophilized mixture.

11. The kit of claim 8, characterized in that the GNPs, target specific un-catalyzed nucleic acid substrate and the target specific pre-catalytic nucleic acid subunits are in a lyophilized mixture.

12. The kit of claim 8, wherein the kit further comprises ingredients necessary for optimal activity of the catalytic domain.

13. The kit of claim 8, characterized in that the kit further comprises a thin layer chromatography (TLC) plate.

* * * * *